(12) United States Patent
Murphy et al.

(10) Patent No.: US 9,553,896 B2
(45) Date of Patent: *Jan. 24, 2017

(54) SYSTEM AND METHOD FOR CONTROLLING ELECTRONIC COMMUNICATIONS

(71) Applicant: Veeva Systems Inc., Pleasanton, CA (US)

(72) Inventors: Timothy S. Murphy, Berkeley, CA (US); John Howard, San Ramon, CA (US)

(73) Assignee: VEEVA SYSTEMS INC., Pleasanton, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/613,293

(22) Filed: Feb. 3, 2015

(65) Prior Publication Data

US 2015/0150098 A1 May 28, 2015

Related U.S. Application Data

(63) Continuation-in-part of application No. 14/271,134, filed on May 6, 2014, now Pat. No. 9,055,023.

(60) Provisional application No. 61/820,029, filed on May 6, 2013, provisional application No. 61/828,034, filed on May 28, 2013.

(51) Int. Cl.
*H04L 9/32* (2006.01)
*H04L 29/06* (2006.01)
*G06F 19/00* (2011.01)
*H04L 12/58* (2006.01)

(52) U.S. Cl.
CPC ............. *H04L 63/20* (2013.01); *G06F 19/322* (2013.01); *H04L 51/063* (2013.01); *H04L 51/12* (2013.01)

(58) Field of Classification Search
CPC .......... G06F 21/30; G06F 21/31; H04L 63/08; H04L 63/10; H04L 63/101; G06Q 10/107; G06Q 30/0601
USPC   726/2–7, 26–30; 713/193; 709/206; 705/26, 705/43, 35, 14, 58
See application file for complete search history.

(56) References Cited

U.S. PATENT DOCUMENTS

| | | | | |
|---|---|---|---|---|
| 6,463,417 | B1 * | 10/2002 | Schoenberg | G06F 19/322 705/2 |
| 7,613,620 | B2 * | 11/2009 | Salwan | G06F 19/322 600/300 |
| 7,647,320 | B2 * | 1/2010 | Mok | G06Q 50/22 705/2 |
| 7,730,142 | B2 * | 6/2010 | LeVasseur | H04L 63/306 709/204 |
| 7,870,204 | B2 * | 1/2011 | LeVasseur | H04L 63/306 709/204 |
| 9,055,023 | B2 * | 6/2015 | Murphy | H04L 51/063 |
| 9,171,344 | B2 * | 10/2015 | Yu | G06Q 10/06 |

* cited by examiner

*Primary Examiner* — Hosuk Song

(57) ABSTRACT

The approved email generation system described is capable of producing email communications between user and customer by using approved email templates and content that have been aligned with customer information regarding access to such content. The approved email template comprises data pulled from a record for a medical inquiry and a window for receiving free text responding to the medical inquiry. Once the approved email has been generated, the content may be verified again for accuracy and validity and the free text may be checked for any unapproved word before being delivered to the customer.

20 Claims, 22 Drawing Sheets

XYZ Analytics

Home   My Accounts   My Schedule   My Samples   Analytics   Cycle Plans   Medical Events

Search

Search All ▾

[ Go! ]

☐ Limit to items I own

Advanced Search...

Create New... ▾

Recent Items
- Tim Mills
- MCC-000000014
- Judy Miller
- Joe Michaels
- Suzy Matthews
- Jess Mills
- Family Practice, PC
- John Smith
- Clean Template - Hello Coldcap
- SE-0048

🗑 Recycle Bin

Account
Dr. Tim Mills

<< Back to List: Users

Account Detail                                [ Edit ]

▾ Account Information
| | |
|---|---|
| Name | Dr. Tim Mills |
| Middle | |
| Suffix | |
| Preferred Name | |
| Territories | 103 |
| Language | French |

▾ Contact Information and Preferences
| | |
|---|---|
| Phone | |
| Email | tim.mills@bobssystems.com |

▾ Profile Information
| | |
|---|---|
| Investigator? | ☐ |
| KOL? | ☐ |

▾ Ratings and Evaluations

[ Common ] ✏

| | Awareness |
|---|---|
| Anvil | ☐☐☐☐ |
| Birdvana | ☐☐☐☐ |

| Logged in as Jane Doe (jdoe@vv.pm2.tim) | Sandbox: Ti... |

Jane Doe ▼   Help & Training   vBioPharma ▼

Approved Documents   Sent Email   Multichannel Consents   +

Customize Page | Printable View | Help for this Page

Sent Email [ 5+ ] | Multichannel Consents [ 5+ ] | Cycle Plan Targets [ 0 ] | Addresses [ 1 ] |
Affiliations [ 0 ] | Calls [ 0 ] | Call Samples [ 0 ] | Account Plans [ 0 ] | Medical Inquiries [ 0 ]

[ Record a Call ]  [ Account Summary ]  [ Calendar ]  [ Email Opt In ]  [ Send Email ]

Account Record Type   Professional
Primary Parent
Credentials   MD
Specialty (?)
Spend Status   ⊘
Spend Amount   200
Restricted Products
Approved Email Consent PDRP Opt-Out   ☐
PDRP Opt-out Date
Website

ME #

| Segment | Movement |
|---------|----------|
|         | ✎        |
|         | ✎        |

FROM FIG. 13a

SYSTEM AND METHOD FOR CONTROLLING ELECTRONIC COMMUNICATIONS

CROSS-REFERENCE TO RELATED APPLICATIONS

The present application is a continuation-in-part of U.S. nonprovisional patent application Ser. No. 14/271,134, filed on May 6, 2014, entitled System and Method for Controlling Electronic Communications, which claims priority to provisional patent application No. 61/820,029, filed May 6, 2013 and 61/828,034, filed May 28, 2013, both entitled "System and method for controlling electronic communications." All of these provisional and nonprovisional patent applications are hereby incorporated by reference herein for all purposes.

TECHNICAL FIELD

The present application relates generally to systems and methods that provide for sending approved content to electronic communications recipients, including methods and systems for building the approved content and generating the approved messages for electronic communications such as email.

BACKGROUND

In certain fields, the ability to achieve the efficiencies associated with modern electronic communications such as email has been hampered by the risks (regulatory and otherwise) of sending such electronic communications. An example of one field that has been so limited has been the pharmaceutical sales industry, where sales reps typically are restricted from sending email communications to prescribing doctors because of the enormous risks that can flow from unapproved, uncontrolled messages. For example, a careless rep or other personnel might send an email to a subscribing doctor suggesting off-label uses for a drug. This could end up exposing the company employer (e.g., a pharmaceutical company) to regulatory penalties or other legal liabilities.

SUMMARY

Embodiments disclosed in the present document provide a machine-implemented method for generating approved emails. The method comprises: establishing a controlled content repository, the controlled content repository being securely and controllably accessed; establishing an access protocol for the controlled content repository, whereby approved content is stored in the controlled content repository according to the access protocol and whereby the access protocol comprises at least one set of alignment rules for determining if a first item of approved content within the controlled content repository can be made available to a first customer via an electronic message; storing the approved content within the controlled content repository, the approved content further being accessible according to the established access protocol; aligning the approved content within the controlled content repository with information from an information management system; and generating an electronic message according to the established access protocol. The electronic message responds to a medical inquiry.

BRIEF DESCRIPTION OF THE DRAWINGS

For a more complete understanding of the present application and its advantages, reference is now made to the following description taken in conjunction with the accompanying drawings, in which like reference numbers indicate like features.

FIGS. 10a-c illustrate screenshots of an example approved email template with user-selected hyperlinks to approved content included within the body;

FIG. 11 illustrates a screenshot of an example "Preview" screen, from which the user may view the approved email in the format in which it is viewable by the recipient;

FIGS. 13a-b illustrate screenshots of one embodiment of the customer profile information screen wherein users may have access to information regarding approved email communication history with the customer;

Although similar reference numbers may be used to refer to similar elements for convenience, it can be appreciated that each of the various example embodiments may be considered to be distinct variations.

Figure 1:
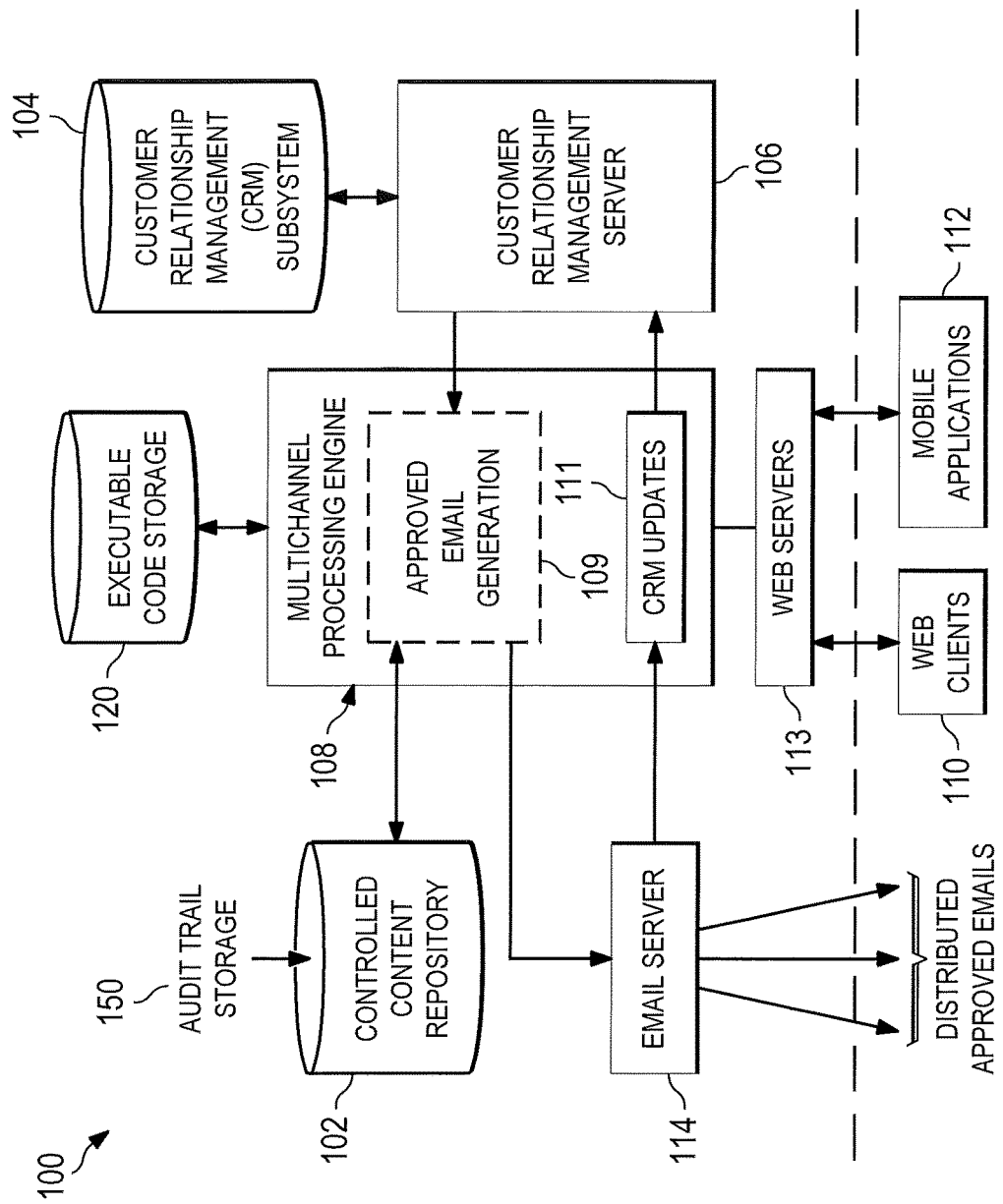
FIG. 1 illustrates an exemplary architecture for managing the building and sending of approved electronic communications.

The present embodiments will now be described hereinafter with reference to the accompanying drawings, which form a part hereof, and which illustrate example embodiments which may be practiced. As used in the disclosures and the appended claims, the terms "embodiment" and "example embodiment" do not necessarily refer to a single embodiment, although it may, and various example embodiments may be readily combined and interchanged, without departing from the scope or spirit of the present embodiments. Furthermore, the terminology as used herein is for the purpose of describing example embodiments only, and are not intended to be limitations. In this respect, as used herein, the term "in" may include "in" and "on," and the terms "a," "an" and "the" may include singular and plural references. Furthermore, as used herein, the term "by" may also mean "from," depending on the context. Furthermore, as used herein, the term "if" may also mean "when" or "upon," depending on the context. Furthermore, as used herein, the words "and/or" may refer to and encompass any and all possible combinations of one or more of the associated listed items.

DETAILED DESCRIPTION

Embodiments disclosed in the present application allow for control of email content for communications between system users and email recipients (customers) by providing for a system and method for generating an "approved email" communication. Users may access a list of email templates which have been pre-generated with approved content and then aligned with various customer attributes such as regulatory limitations, customer preferences and demographic information in order to ensure compliant and tailored communication between the user and the customer.

Such controlled email or other electronic communication generation occurs at an interface between a repository of approved content items and templates along with customer relationship management (CRM) information including customer profile information and parameters including customer preferences and regulatory limitations or fields that can be used to facilitate compliance with regulatory limitations. The system is capable of generating warning notices to users when content and customer access do not align and users may choose various actions to address the warning notices such as excluding certain customers from the communication or changing email content. The customer information is from a customer relationship management subsystem.

In disclosed embodiments, intelligent and flexible updating of records may be provided within the customer relationship management subsystem, including such approaches as communicating with third-party systems and sources in order to verify and update customer information in an effective and timely manner, such as by using the collective information gained by managing a cloud-based system/Software-as-a-Service (SaaS) system on behalf of multiple company customers for the disclosed embodiments.

After approved emails are constructed by the user, the content contained within the approved email may be once again checked for accuracy and validity by the system before release to the email server. When a customer accesses content within an approved email, the customer is directed to a customer portal through which the content is accessed. The customer may be only allowed access to the most current version of the approved content within the content repository. In this manner, the content received and viewable by the customer has been verified in real-time as being compliant, approved content.

FIG. 1 is a system overview illustrating an embodiment of a controlled email communication system 100. The presently disclosed embodiment comprises a controlled content repository 102, a Customer Relationship Management (CRM) server 106, and a multichannel processing engine 108. The customer relationship management server 106 may provide access to a customer relationship management subsystem 104, and the multichannel processing engine 108 may be coupled to an email server 114. In one embodiment, the customer relationship management subsystem 104 and/or the email server 114 may be operated by a third party. The multichannel processing engine 108 may be accessed by users such as company sales representatives through web clients 110 or through mobile apps 112 (such as iOS, Android, Blackberry, or Windows Mobile systems), communicating with the multichannel processing engine 108 through web servers 113. Although the users may be described in the present application as being company sales representatives, this particular described embodiment is not intended to limit the generality of the claims that may eventually issue in patents stemming from the present disclosure.

The controlled content repository 102 is designed to have a process for developing approved content that is sharable across multiple users, such as shareholders, reviewers, managers, marketing personnel, sales representatives, etc. The content generated in the controlled content repository 102 may be accessed on a regulated basis and used to generate approved electronic communications. This regulated basis may be determined, in part, by the company as a whole and additionally by interaction with data from the customer relationship management subsystem 104, described in further detail below. In one embodiment, approved content, customer profile information, customer preferences, and regulatory limitations and requirements may be stored in a table in the controlled content repository 102. In addition to storage and development of content, the controlled content repository 102 may also store an audit trail, tracking exact content of communications as they were sent by the user, as well as metadata about the communications and information regarding the content accessed by customers.

The customer relationship management subsystem 104 contains all contact information that may be available to users. In addition to storage of contact information, the customer relationship management subsystem 104 may also be capable of storing configurations regarding specific preferences, regulatory limitations and requirements, and other fields that will facilitate the generation of appropriate approved electronic communications, in general or on a by-recipient basis. These preferences and/or requirements include both the preferences of the user (e.g., maintaining account lists) as well as the preferences of the enterprise (e.g., employers of the users), discussed in further detail below. In some examples, the approved content and email templates may be pre-processed and stored in the controlled content repository 102 and provided to the multichannel processing engine 108 during the process for generating an approved email. In other examples, the customer relationship management subsystem 104 may have a content management subsystem and may provide the approved content and the templates.

In this embodiment, the customer relationship management subsystem 104 is capable of communication with multiple sources through the customer relationship management server 106 or through other channels to maintain a current and accurate collection of information regarding customer accounts. The interface with the multiple sources can be, for example, through an Applications Programming Interface or API, as the API interface will allow compatibility with a flexible array of third-party provider servers. The information being updated may include, but is not limited to, licensing information, area of practice, and location of the various customer contacts. In this manner, the customer relationship management subsystem 104 pulls the approved version of what represents an account or physician, which then pulls from multiple networks to ensure that the information regarding an account is up-to-date. The customer relationship management subsystem 104 may also be used to determine the type of domain an email communication is delivered through. A customer in Spain may receive an email from "CompanyX.es," whereas a customer in Germany would receive the same email from "CompanyX.ge." This may allow for additional branding options for the company controlling and sending the electronic communications.

With further reference to the customer relationship management subsystem 104, this system may be a cloud-based customer database that provides a central access to store and distribute consistent data across customer companies as well as their possible third-party partners and agencies that are used to keep this data updated. This system can provide standard data formats and provide an easy and automated way for customers to have access to coordinated and frequently updated CRM data and to use that coordinated data for sending approved electronic communications in accordance with the system described herein.

In an embodiment, the multichannel processing engine 108 is responsible for combining the customer account information from the customer relationship management subsystem 104 with content available from the controlled content repository 102. Within the customer relationship management subsystem 104, customer accounts may be assigned a set of alignment rules which determine specific pieces of content that are available for use from the controlled content repository 102. The multichannel processing engine 108 may apply these rules and supply the user with a list of approved email templates and pieces of content that may then be used to construct an approved email communication. Approved email generation occurs within the multichannel processing engine 108 according to executable code computer instructions stored in executable code storage 120.

The executable code comprises computer readable instructions stored on the computer readable medium (the code storage medium 120). The executable code storage 120 is in communication with the various computing machines in the system 100 such as the customer relationship management server 106 and the multichannel processing engine 108. The same or another executable code storage 120 may be accessed by the previously described components of the controlled content repository 102 for providing separate computer readable code for operating upon by processing machines in that system. In all cases, the code is programmed to perform the functions that are described in the present embodiments and/or additional functions according to system design needs.

Communication between the multichannel processing engine 108 and the customer relationship management subsystem 104 may occur via the customer relationship management server 106, which acts as an interface between the two. The customer relationship management server 106 may act solely as an entry and exit point for the customer relationship management subsystem 104. The user may access the multichannel processing engine 108 through either a Web Client 110 or through the mobile apps 112 (such as iOS, Android, Blackberry, or Windows Mobile systems).

Figure 2:
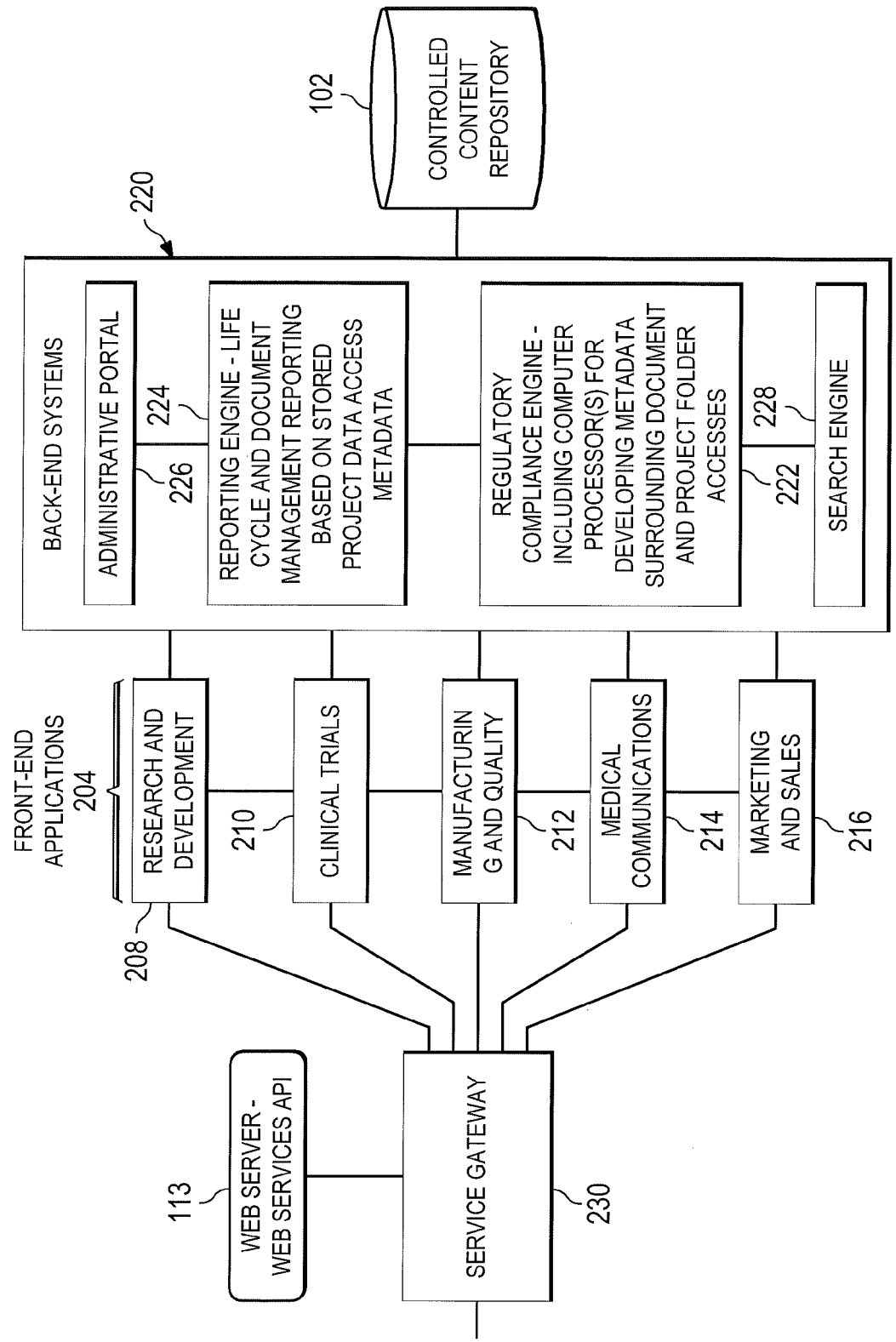
FIG. 2 illustrates an example architecture for the content repository of FIG. 1 in which content is built and organized in a controlled manner that facilitates efficient content generation.

FIG. 2 provides a description of the controlled content repository 102 with additional specific applications and interfaces connected thereto. In an embodiment, this controlled content repository 102 is a cloud-based or distributed network based system for consolidating an enterprise's data, oftentimes integrating multiple content repositories in an enterprise into a single system having coordinated control, measuring, and auditing of data creation, access and distribution.

In an embodiment of the controlled content repository 102 for the life sciences industry, as illustrated in the figure, this repository 102 can include specific data collections for the following areas and/or business process-specific front-end applications 204:

The Research & Development (R&D) front end application 208 provides for an aggregation of materials in support of research and initial clinical trial submissions through building organized and controlled content repositories within the controlled content repository 102. Elements that can be stored, organized, and managed through this front end include submission bills of materials, Drug Information Association (DIA) reference models support, and submission-ready renderings. This front end 208 is designed to provide an interface to the controlled content repository 102 whereby researchers, contract research organizations (CROs), and other collaboration partners can access and/or distribute content through a single controlled document system.

The clinical trials front-end application 210 provides for faster and more organized access to trial documents and reports, while supporting seamless collaboration between sponsors, CROs, sites, investigators and other trial participants. Specific features both ease study and site administration as well as support the DIA trial master file (TMF) reference model. Having this front-end application providing access to the controlled content repository 102 further provides for efficient passing off of controlled content repository content between this phase and other phases of the life sciences development process.

The manufacturing and quality application 212 enables the creation, review, approval and distribution of controlled documents across the organization and with external partners in the context of materials control and other manufacturing elements. The application 212 provides functionality in support of the manufacturing process including watermarking, controlled print, signature manifestation and "Read and Understood" signature capabilities. The documents and metadata associated with this process is managed and stored in the controlled content repository 102 whereby it can be assured that the related documents are not distributed in contravention of law and company policy.

The medical communications application 214 provides for communications with medical facilities, including call center access, integration, and interface functionality. Particular access control features and metadata associated with this application 214 include expiration and periodic review elements, multi-channel support, global documents and automatic response package generation through the controlled content repository 102.

The marketing and sales application 216 provides an end-to-end solution for the development, approval, distribution, expiration and withdrawal of promotional materials.

Specific features include support for global pieces, approved Form FDA 2253 (or similar international forms) form generation, online document, and video annotation, and a built-in digital asset library (DAL). Again, the communications may be through the controlled content repository 102.

In disclosed embodiments, there are provided a number of back-end system applications 220 that provide for the management of the data, forms, and other communications in the controlled content repository. For example, the back-end systems applications 220 may include a regulatory compliance engine 222 to facilitate regulatory compliance, including audit trail systems, electronic signatures systems, and system traceability to comply with government regulations, such as 21 CFR Part 11, Annex 11 and GxP-related requirements. The regulatory compliance engine 222 may include processors for developing metadata surrounding document and project folder accesses so from a regulatory compliance standpoint it can be assured that only allowed accesses have been permitted. The regulatory compliance engine 122 may further includes prevalidation functionality to build controlled content in support of installation qualification (IQ) and/or operational qualification (OQ), resulting in significant savings to customers for their system validation costs.

In further disclosed embodiments, the back-end systems 220 may contain a reporting engine 224 that reports on documents, their properties and the complete audit trail of changes. These simple-to-navigate reports show end users and management how content moves through its life cycle over time, enabling the ability to track 'plan versus actual' and identify process bottlenecks. The reporting engine may include processors for developing and reporting life cycle and document management reporting based on stored project data and access metadata relative to documents, forms and other communications stored in the controlled content repository 102.

In further disclosed embodiments, the back-end systems 220 can include an administrative portal 226 whereby administrators can control documents, properties, users, security, workflow and reporting with a simple, point-and-click web interface. Customers also have the ability to quickly change and extend the applications or create brand new applications, including without writing additional software code.

In further disclosed embodiments, the back-end systems 220 may include a search engine 228 whereby the controlled content repository 102 can deliver simple, relevant and secure searching.

In providing this holistic combination of front-end applications 204 and back-end system applications 220, the various applications can further be coordinated and communicated with by the service gateway 230, which in turn can provide for communications with various web servers and/or web services APIs 113. Such web servers and/or web services APIs 113 can include access to the content and metadata layers of some or all of the various applications 204 and systems 220, enabling seamless integration among complementary systems.

In the context of the described embodiments, the particular features and capabilities integrate with the other elements of the controlled email communication system 100 such that particular features are usable within the various user screens. For example, and without limitation to any other possible combination of features, in the below-described description of generating an approved electronic communication, the above-described search portal can be used to search for approved attachments (i.e. content) within the controlled content repository 102 which may be then attached to one of the template emails being prepared for sending to a customer. And the synergy of combining these particular systems is that the generation of the controlled content can be done in a controlled fashion such that the approved content can be sent to customers with greater confidence in the integrity of the data being sent.

Figure 3A:
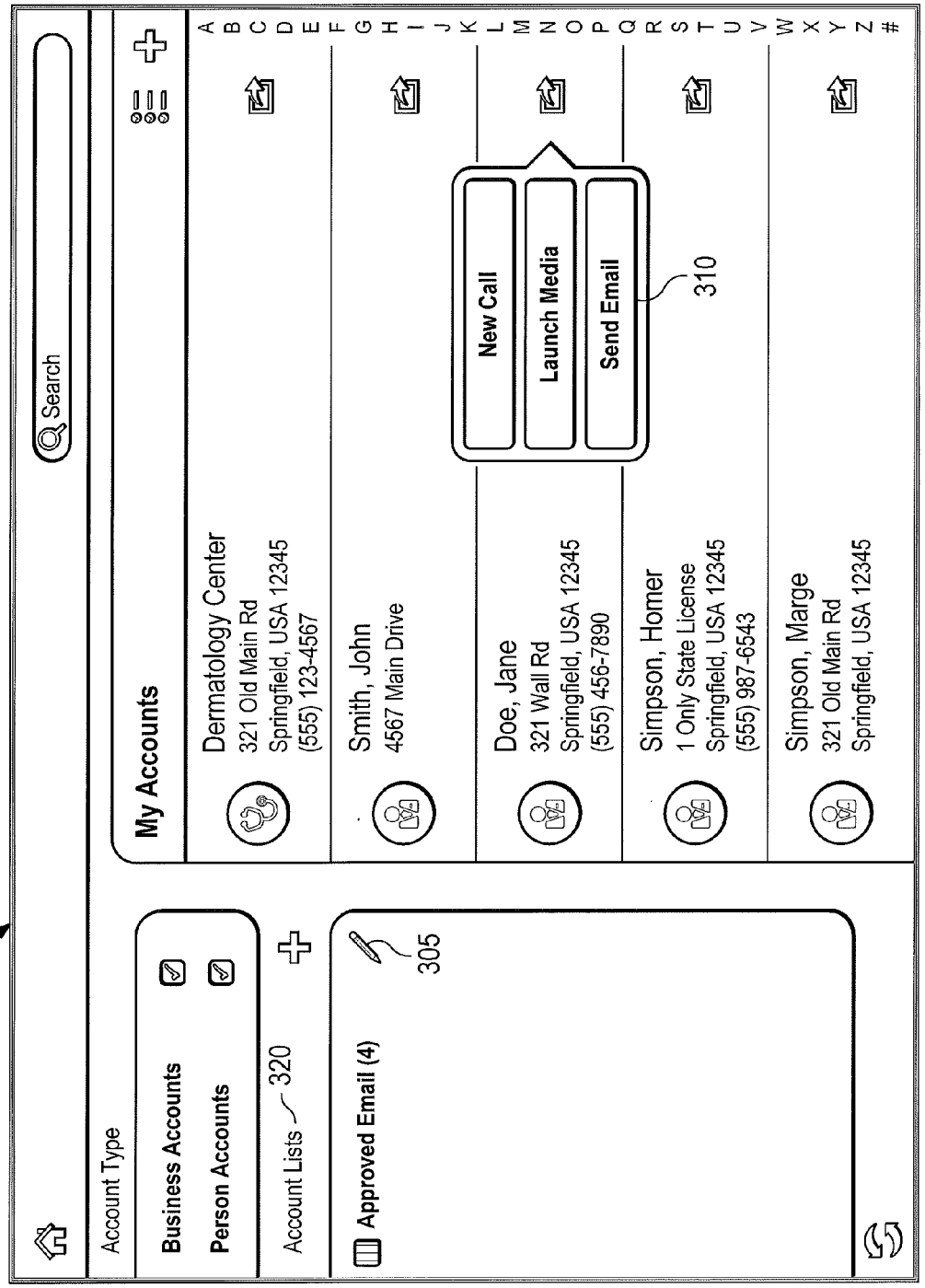
FIG. 3a illustrates a screenshot showing one embodiment of the "My Accounts" option where the user may access personalized customer mailing lists.

FIG. 3a illustrates an embodiment screenshot 302 of a "My Accounts" interface in a web-based or mobile interface within a web-based system 110 or mobile system 112 (see FIG. 1). From this screen 302, a user may select an individual account from a list of existing physician or other clinical accounts within the customer relationship management subsystem 104. By selecting a specific individual account from the "My Accounts" screen 302, the user can be taken to a screen containing current contact information for the selected account as stored in the customer relationship management subsystem 104. From this screen, users may begin constructing an approved email to the individual customers by selecting a "Compose Email" link on the screen. In this embodiment, there are additional options within the web-based or mobile application 110, 112 for sending an individual customer an approved email. From the "My Accounts" screen 302 shown in FIG. 3a, the user may also click on or mouse over the "Action" sheet shown in this embodiment to the right of the contact name to get a pop-up window and select a "Send Email" link 310 in the pop-up window. The user may click on a link 305 to update information of the accounts.

Figure 3B:
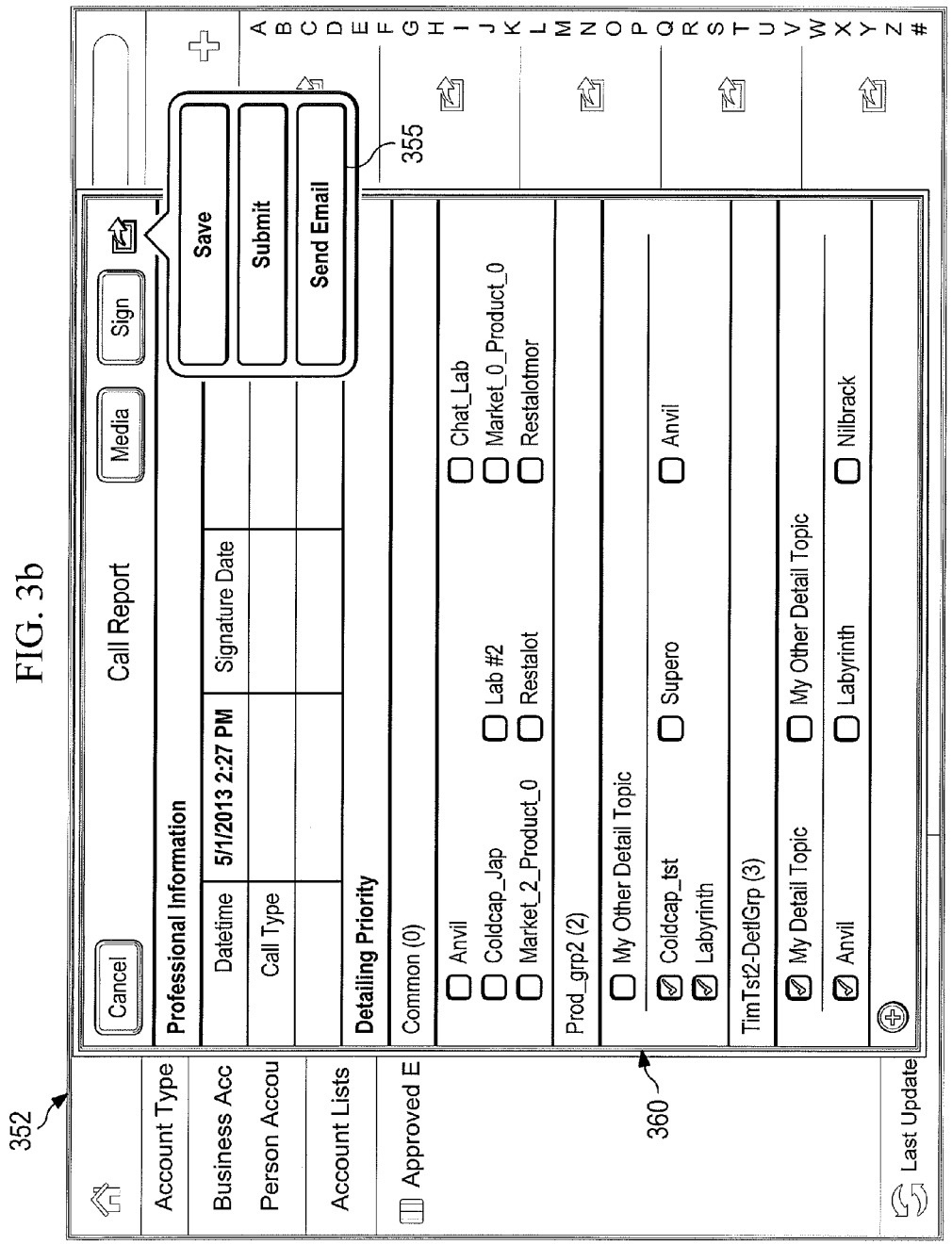
FIG. 3b illustrates a screenshot showing an embodiment of starting to build an approved email from a content page.

A user may also begin constructing an email from a content page, e.g., when the user is viewing a document or a video on his screen. FIG. 3b illustrates an embodiment screenshot 352 of a "Call Report" interface in a web-based or mobile interface within a web-based system 110 or mobile system 112 (see FIG. 1). While viewing a Call Report 360 on screen 352, a user may decide to send content related to some topics in the Call Report. The user may click on or mouse over the "Action" sheet next to the "Sign" link shown in this embodiment to get a pop-up window and then select a "Send Email" link 355 in the pop-up window. After that, the screenshot 302 may be displayed for the user to build an approved email. Because the described system including the controlled content repository 102 provides for a coherent and controlled access to the approved content for email communications, it can be made quite flexible as to providing consistently formatted and approved content from various applications and/or specific screenshots within applications.

Figure 4:
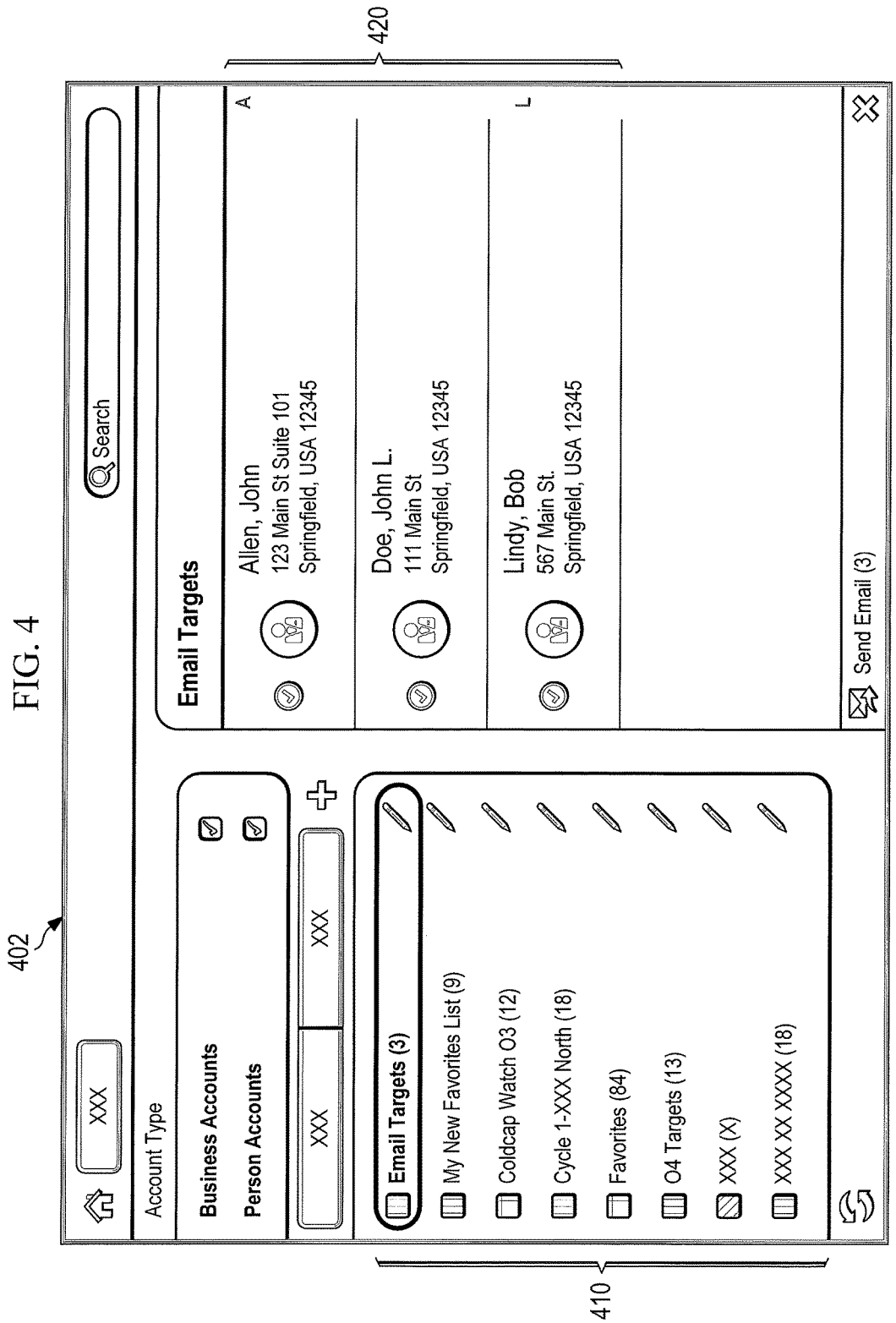
FIG. 4 illustrates a screenshot showing one example of the "Email Targets" option in the mobile application (or web application) from which users may select individuals from the mailing list as recipients of an approved email.

Referring now to FIG. 4, by selecting the "Account Lists" 320 on the left hand side of the screen in FIG. 3a, users may access personally or institutionally pre-constructed lists 410 of individual customers as configured in the customer relationship management subsystem 104. From this screen 402, the user may also select a number of individual customer accounts 420 with whom they wish to communicate. Once desired customers have been selected from the list, which could include the selecting of all customers in the list, the user may begin building an approved email to the selected customers through the web-based or mobile client application 110, 112. The email may be constructed within the multichannel processing engine 108 from the accessible content provided by the controlled content repository 102 which has been aligned with the customer information provided by the customer relationship management subsystem 104.

Figure 5:
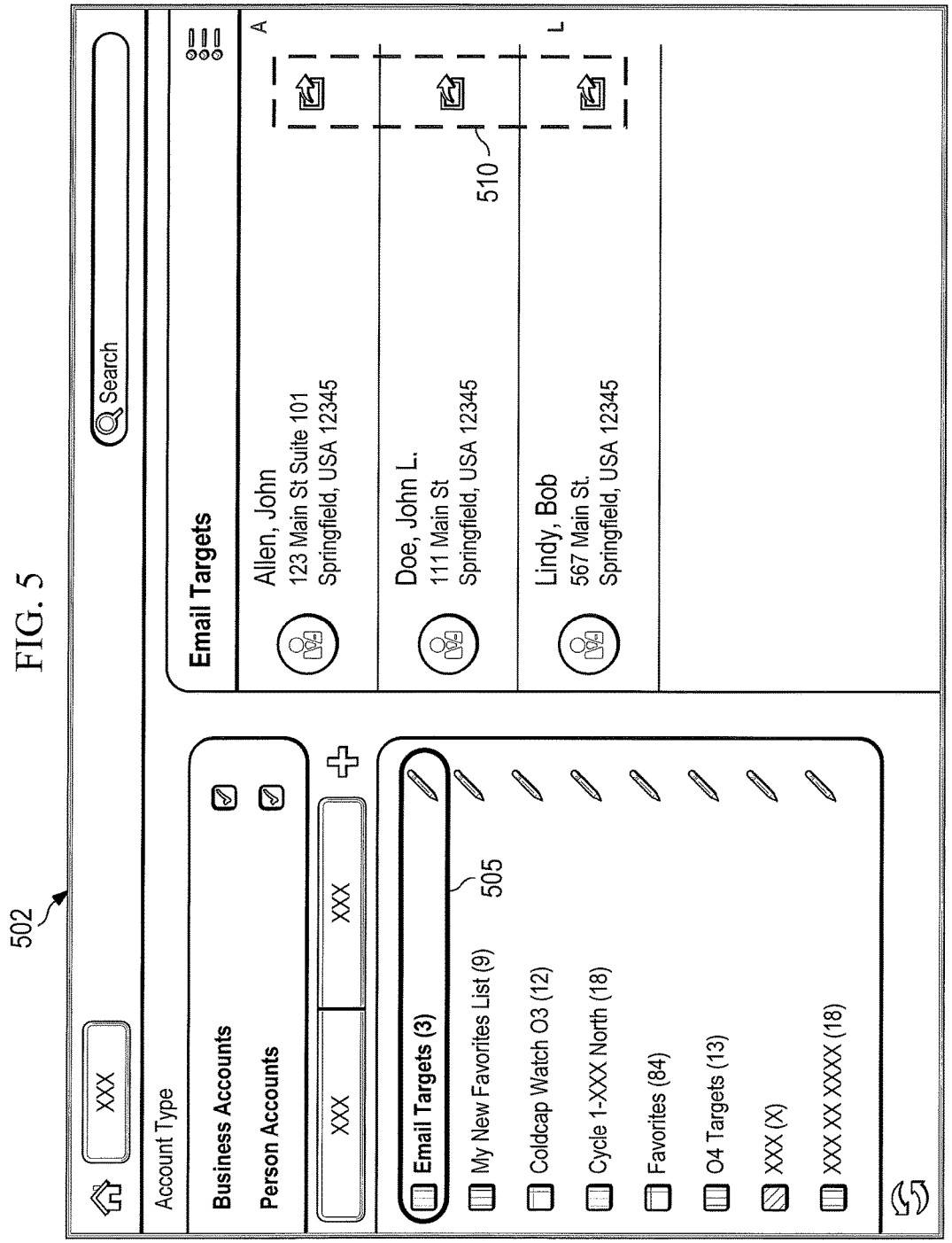
FIG. 5 illustrates a screenshot of an example "Email Targets" screen with individual email targets selected to receive an approved email.

FIG. 5 illustrates an exemplary screenshot 502 in which the user begins constructing the approved email by selecting an "Email Targets" link 505. The link icon may also contain the number of selected customers in parentheses. In this embodiment, the "Send Email" links 510 appear after the customer selection of the "Email Targets" link 505.

Figure 6:
FIG. 6 illustrates a screenshot of one embodiment of an "Email Template" selection screen where the user may choose one or more customer-aligned templates to generate approved emails to selected customers.

Shown in FIG. 6, by selecting the "Send Email" link, the user may access the "Email Generation Wizard." From this screen 602, a user may access pre-approved, controlled email templates 604 that are available and approved for the specific group of customers selected. From this approved list, the user may select multiple templates. After desired templates are selected, individual tabs appear at the top of the screen and within each tab is a separate approved email which may be sent to the selected customers.

Figure 7:
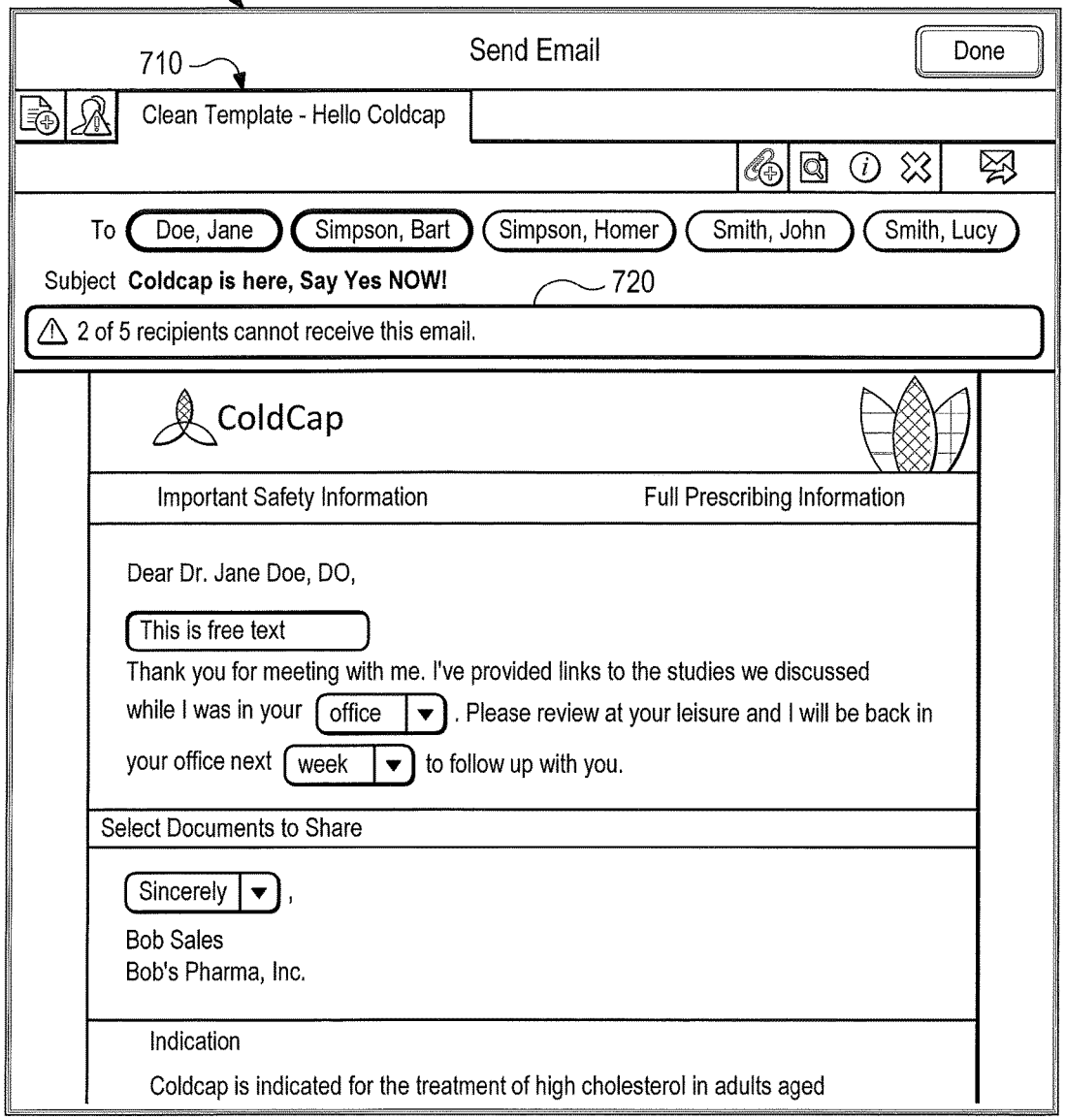
FIG. 7 illustrates a screenshot of an example approved template for email generation with an example warning icon indicating that one or more of the email recipients is unapproved to receive the content within the template or content attached to the template email.

The user may access an individual template, as shown in the screenshot 702 of FIG. 7, by selecting the appropriate tab 710. The template may also display a warning icon 720, shown in the top left of FIG. 7, which indicates that one or more of the selected individuals may be restricted from receiving the chosen template with its current content. This warning is generated from information contained within the customer relationship management subsystem 104. The user may select this icon 720, which generates a pop-up window 802 containing specific warning information for all potential recipients who may be currently restricted from receiving the content, shown in FIG. 8. Recipients may be removed from the email list on this screen by selecting the appropriate icon.

Figure 8:
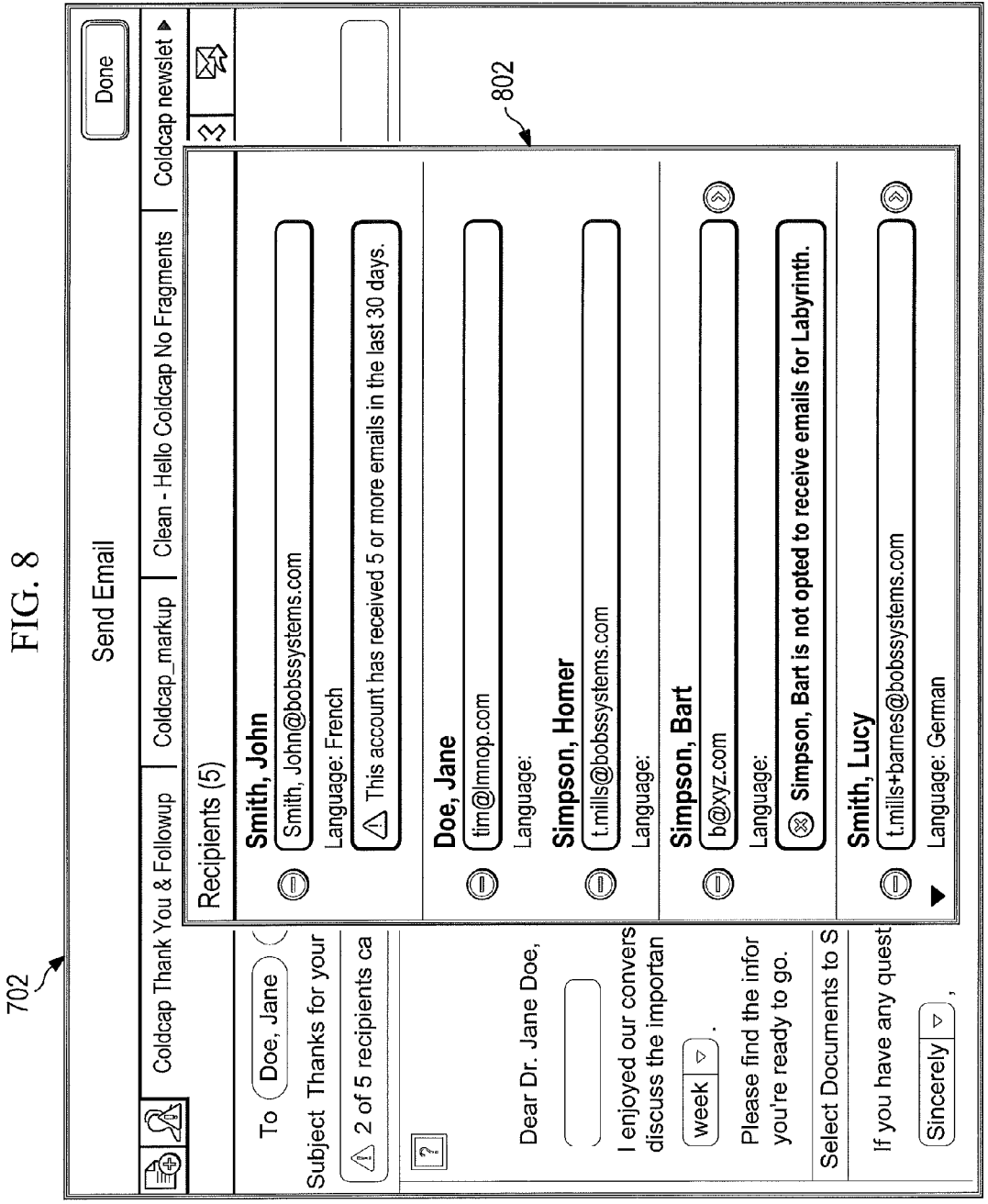
FIG. 8 illustrates a screenshot of example pop-up screen detailing the reasons why individual customers may not be approved to receive the content.

Warnings generated on the pop-up screen 802 illustrated in FIG. 8 may appear for reasons that include, but are not limited to, regulatory limitations, customer preferences, demographic information, a customer "opt-out" option where the customer has requested to not have the content delivered; the absence of a customer "opt-in" option where the customer may not receive the communication without prior approval; or that the most current information contained within the customer account profile no longer allows access to the current content delivered by the controlled content repository 102. Information regarding regulatory limitations, customer preferences, demographic information, the "opt-in" or "opt-out" status of individual customer accounts is stored within the customer relationship management subsystem 104.

Figure 9:
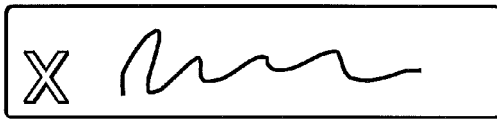
FIG. 9 illustrates a screenshot of one embodiment of the signature capture technology available to users through the mobile application to provide for remote opt-in for electronic communications.

In an embodiment, as shown in FIG. 9, the user may access an "opt-in" request 902 from the recipient of the email through the web-based or mobile client applications 110, 112. In this embodiment, the user may have access to signature capture technology, which allows for instant, remote customer approval along with the appropriate signature 905.

Figure 10A:
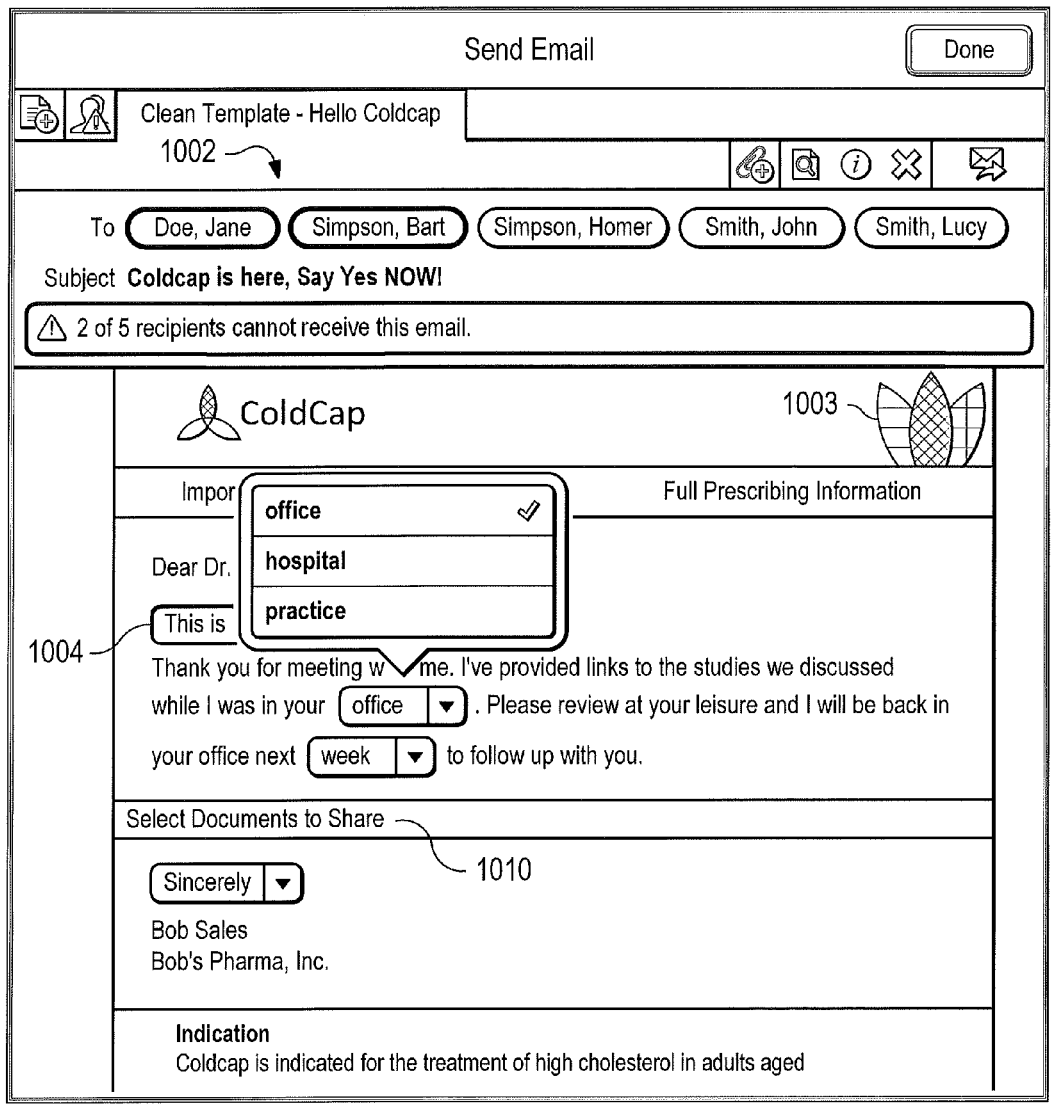

Once all warnings are cleared, or all restricted recipients are removed from the list, the user may once again have access to the approved email template 1002 as illustrated in FIG. 10*a*. Email templates may be either "branded" with imagery 1003 or may be presented in a plain, text-only format, selectable by the user. As illustrated in FIG. 10*a*, the user may have the ability to personalize the email content by free-texting in the text box 1004 supplied within the template. This customizable text box 1004 may also be regulated to ensure compliance by limiting the number of characters that may be typed in the box and by constructing "libraries" of restricted words for each customer that may not be used in the box. The information used to regulate the text box may be accessed from the customer relationship management subsystem 104, and configuration of these regulatory parameters may be designated by both the company, by the specific customer, and/or by specific regulation. Within the approved template, the user may choose from approved content to be included in the body of the email.

Figure 10B:
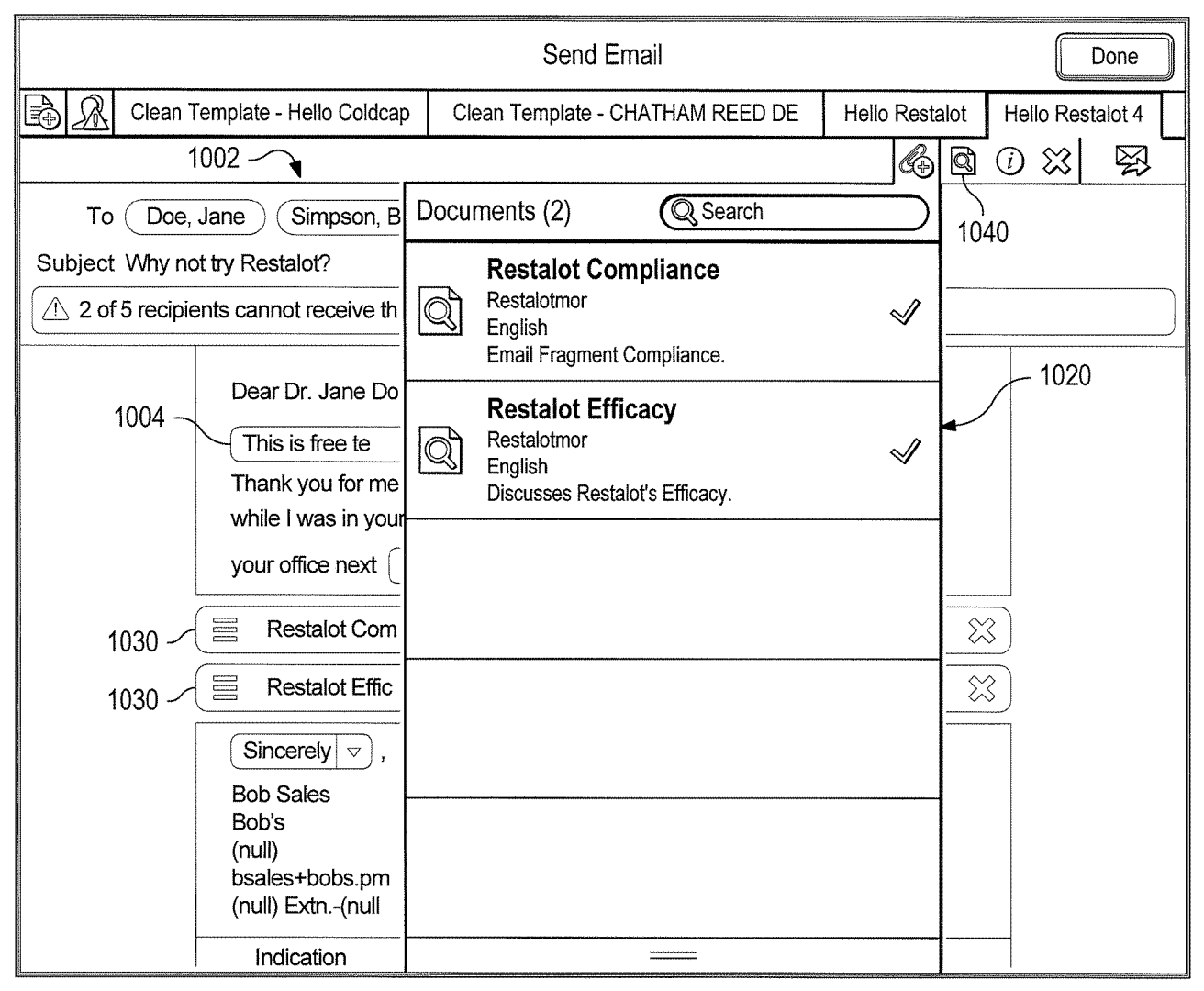

The user may select the "Select Documents to Share" icon 1010 within the template, which generates a pop-up screen 1020 (see FIG. 10*b*) containing a list of approved content from within the controlled content repository 102 that has been aligned with the customer information retrieved from the customer relationship management subsystem 104. From the pop-up screen 1020, the user may select multiple content items to be included within the body in the form of one hyperlink per selected content item. As the content items are selected, they are added to the body of the email as individual tiles 1030 as illustrated in the center of FIG. 10*b*. The list of content items may be rearranged by the user by dragging the tiles into the desired order. The user may preview the approved email on the web-based or mobile applications 110, 112 as it will be received by the customer by selecting the "magnifying glass" icon 1040 located within the template screen. The user may then return to the edit function by selecting an "editing" icon or clicking outside the document selection pop-up screen 1020.

Figure 10C:
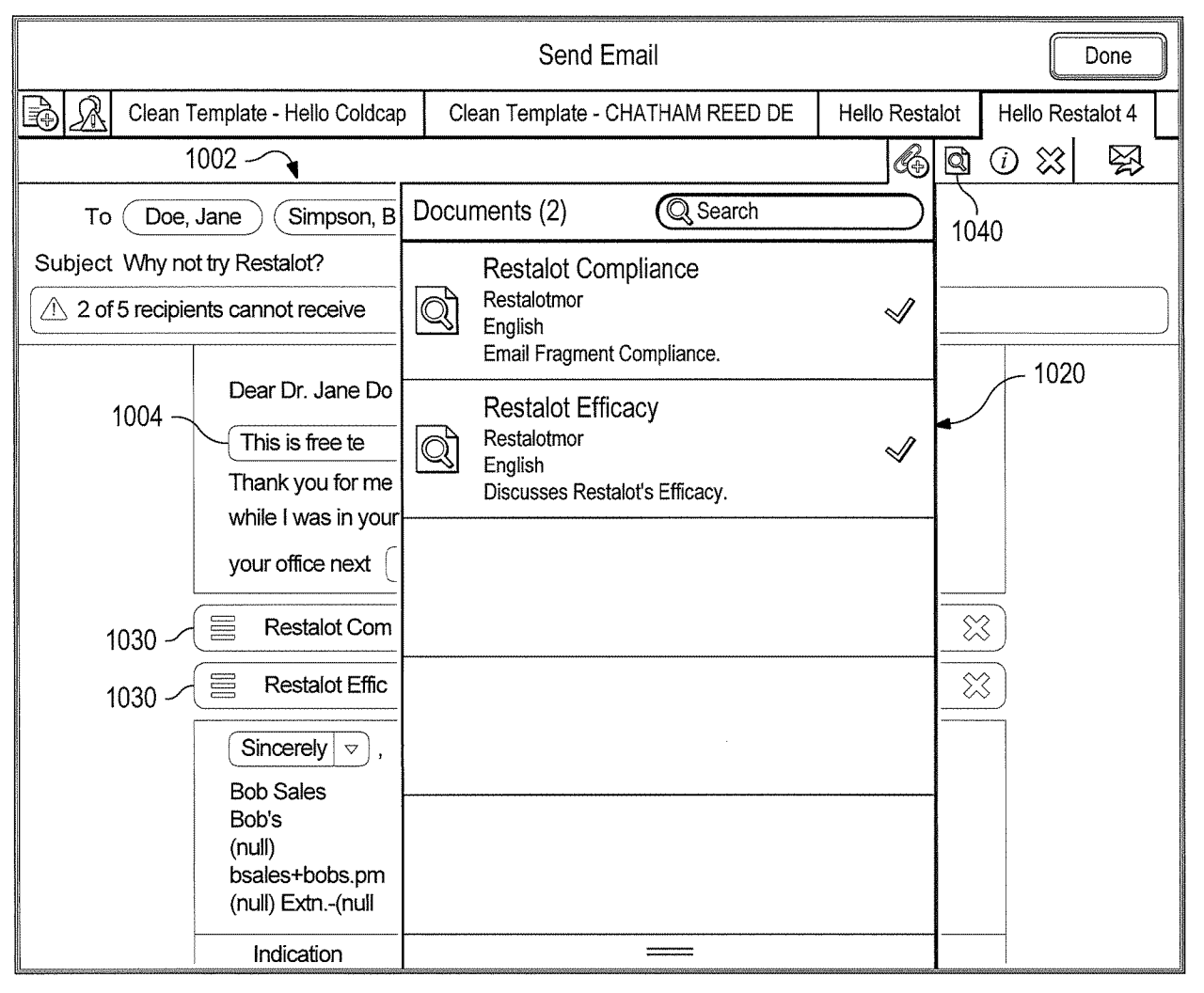

From this continued editing screen 1050 of FIG. 10*c*, the user may also select a customized valediction from a drop-down menu located within the template 1050. The overall approved content authoring system described herein includes selection capabilities that are highly flexible, highly configurable, and may be applicable to any place within the approved email template. The user may then send the email to selected recipients using the "Send" icon 1060 illustrated in FIG. 10*c*.

The communications between the mobile applications 112 or the web clients 110 and the multichannel processing engine 108 may use any communication protocols between a web client and its server, e.g., HttpPost.

In one embodiment, the content contained within the generated email may be once again checked for accuracy and validity by the system just before releasing. Once the approved email is generated in the multichannel processing engine 108 and the user selects the "Send" icon, the communication is then sent to the controlled content repository 102 for final verification of the accuracy and validity of the selected content. The controlled content repository 102 may also store audit trail data 150 which documents and retains information that may include, but is not limited to, recipient information, time stamp data, and the most current version number of any content included within the approved email. The communication is then sent back to the multichannel processing engine 108, where it may be routed through an email server 114 and then delivered to the customer's preferred inbox. The multichannel processing engine 108 may send only enough information to the email server 114 for the email server 114 to create an email, and the email server 114 may create the actual email to be sent to the customer. The email server 114 may collect and distribute the outbound email content, but it may also collect interaction information from the customer regarding clicks, views, and other statistics regarding customer usage. As shown in FIG. 1, this information may then be posted back to the multichannel processing engine 108 as CRM updates 111 and sent through the customer relationship management server 106 to be deposited in the customer relationship management subsystem 104 as information contained within the customer account profile. The email sent may also be stored in the customer relationship management subsystem 104.

Figure 11:
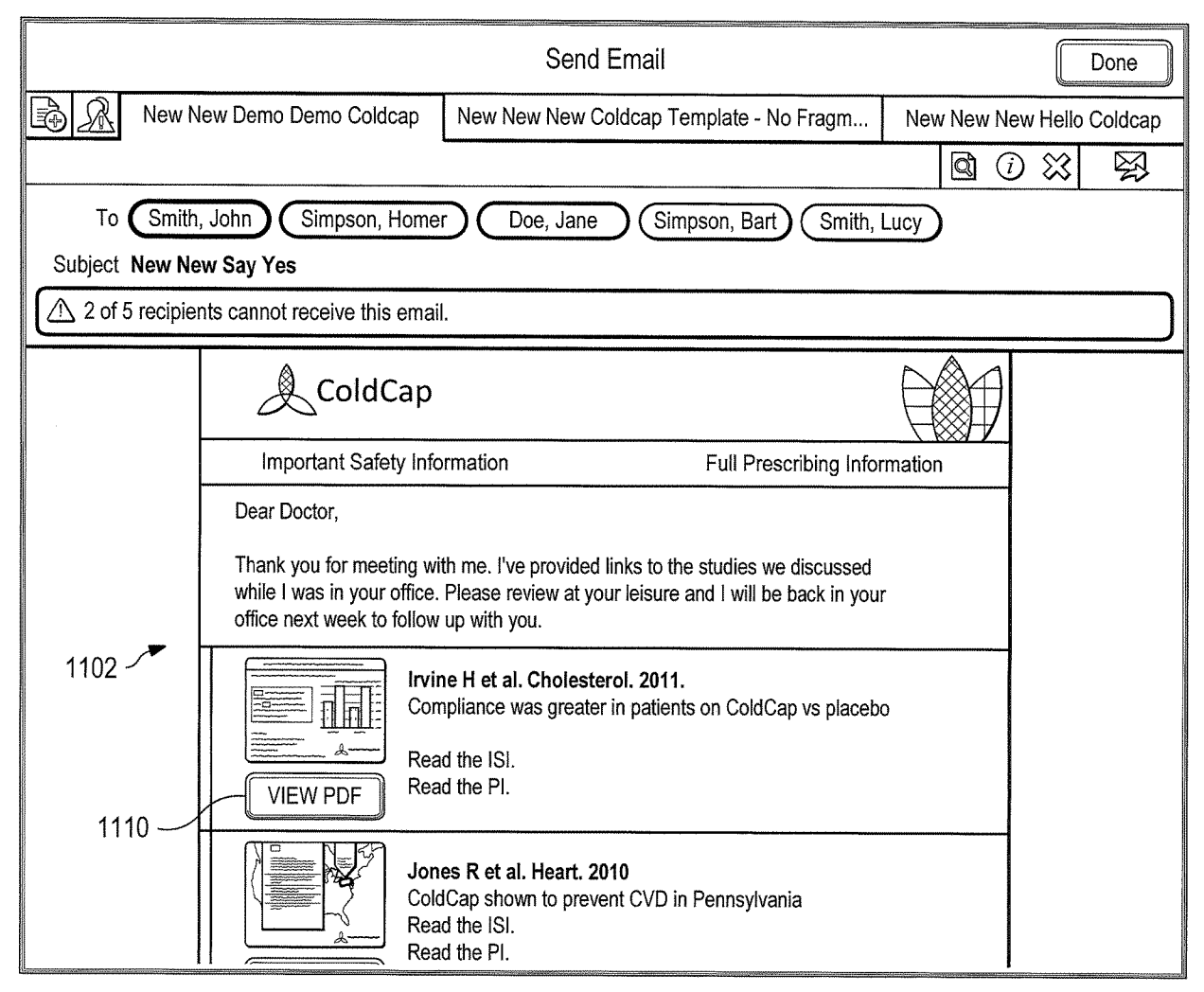
Figure 12:
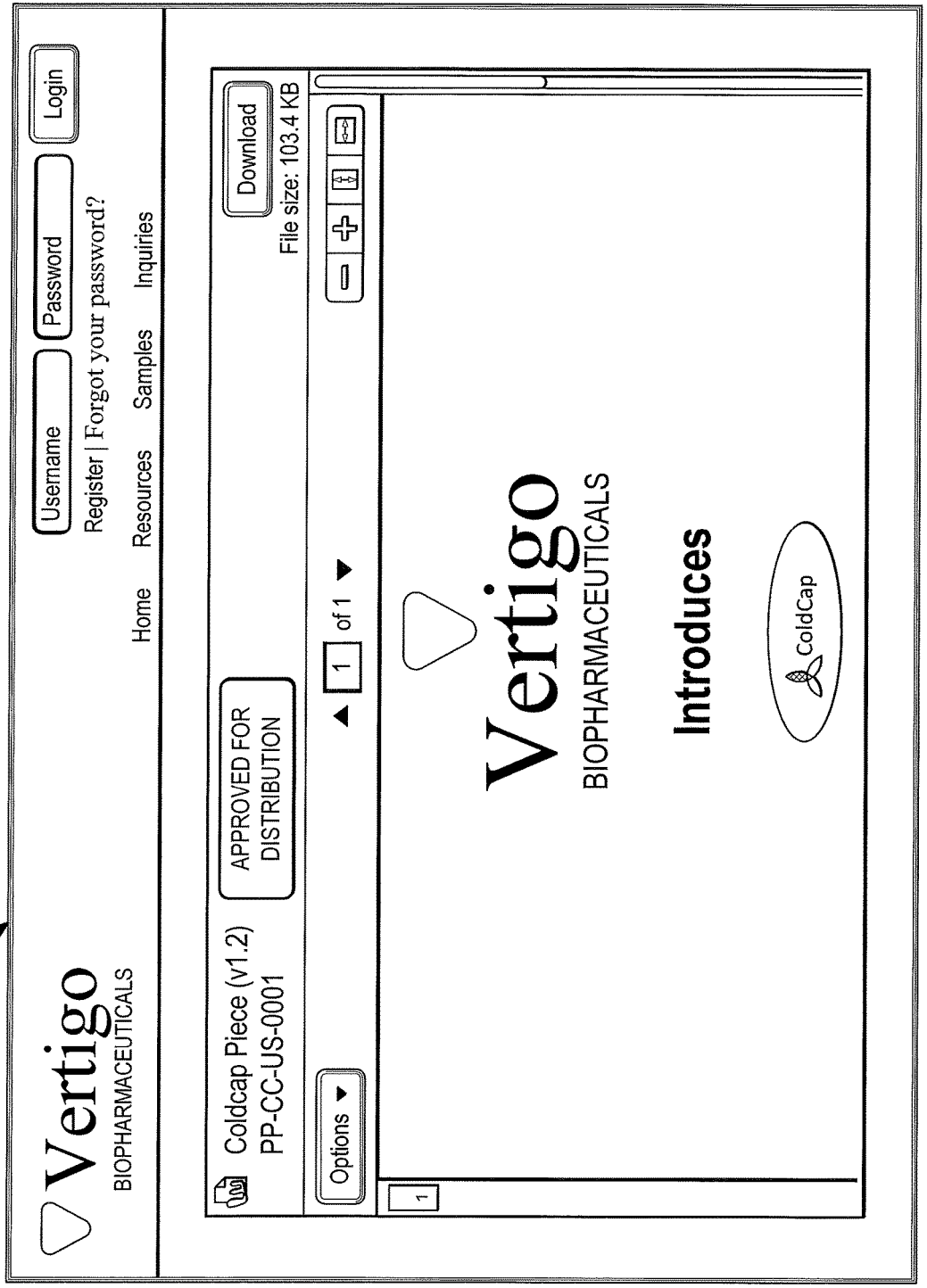
FIG. 12 illustrates a screenshot of an example customer portal through which customers may access approved content from the controlled content repository.

As shown in the approved email preview screen 1102 illustrated in FIG. 11, when an approved email is opened by the customer, the customer may have immediate access to communications as they appeared in the "preview" screens or thumbnails available to the user through the web-based or mobile applications 112. This communication 1102 includes the readable text and a tiled list of approved content hyperlinks, shown in the figure. The recipient may choose to view the content by selecting the appropriate content icon. In an embodiment of the system, the recipient may select the "view pdf" hyperlink 1110 within the email, which will redirect the recipient to the customer portal screen 1202, shown in FIG. 12. Each recipient has the ability to custom-configure the specific URL to be loaded as the "landing page" for clicks from the approved emails.

This arrangement allows for the direction of customers to specific portals. Within the portal 1202, the recipient may view the full text of the content that was included as a tile within the body of the original approved email. The content is accessed directly from the controlled content repository 102 to ensure that the most up-to-date information is displayed when the customer accesses the selected content. If the content has been updated to a newer version since the user constructed the approved email, then the hyperlink included in the approved email will automatically connect the customer to the most up-to-date version of the selected content. Information regarding the content version viewed by the customer may be stored with other pertinent information about the customer experience in the audit trail within the controlled content repository 102. In one embodiment, the controlled content repository 102 may create a token for the approved content to be sent with the approved email. The token may have information about which piece of content to show to the customer, and direct the customer to the right content. In one embodiment, even when the content is updated after the email is sent, the token may direct the customer to the latest version of the content.

Illustrated in FIG. 13a-b is an embodiment of the system that allows the user access to information regarding specific communications. This information is stored in the customer relationship management subsystem 104 along with customer account information. The user may access this information through either mobile apps 112 or through web clients 110. The information available may include, but is not limited to, the number of times the approved email communication has been opened by the customer, the number of clicks executed, type of device used to access the communication, platform used when accessing the content, and location when the communication was viewed.

Figure 14:
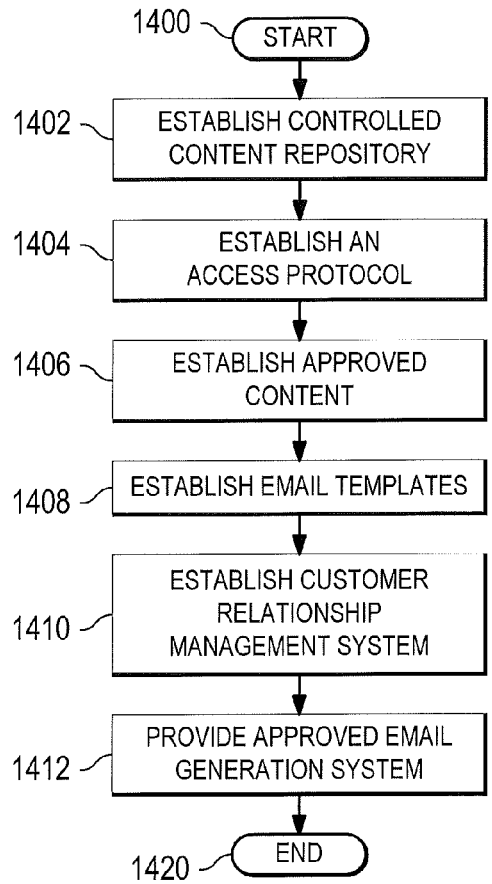
FIG. 14 is a flowchart illustrating the providing and/or provisioning of an approved email system.

FIG. 14 is a flowchart illustrating the building and/or provisioning of exemplary elements of an approved email system in accordance with the embodiments disclosed in the present application. The method starts and block 1400, after which the system builders and/or administrators establish a controlled content repository 102 at block 1402. As described herein, the controlled content repository is designed to be securely and controllably accessed such that only authorized users can build the controlled content therein. To ensure the integrity and security of the controlled content repository 102, an access protocol is established at block 1404. The access protocol may be defined by computer instructions stored in the computer readable memory or executable code storage 120. By the computer instructions stored therein, the multichannel processing engine 108 is thereby able to control access to the controlled content repository 108 in accordance with the principles described in the present application.

At block 1406, one or more users establish approved content to be stored in the controlled content repository 102 under the control of the access protocol established at block 1404 (or as that protocol is later changed or updated). At block 1408, a system designer or other admin establishes or updates email templates that approved content senders can pick and choose from in building approved email content messages. At block 1410, a customer relationship management system is accessed such that the approved emails can be addressed to customer contacts of the enterprise or salesperson for the enterprise who is engaging in the marketing, manufacturing, clinical trials, or other activity described herein. At block 1412, the actual email generation system is provided that interfaces with the approved content, the access protocol, the email templates, and/or the customer relationship management system. This email generation system, or more specifically the multichannel processing engine 108, is accessed by senders of approved email content as described in the present application.

It should be appreciated that as previously discussed, the customer relationship management system 104/106 may be further operable to communicate with multiple sources of information to build a current and accurate collection of information regarding customer accounts. It should also be appreciated that to facilitate such communications, at least one of the multiple sources of information that might communicate with the custom relationship management system 104/106 may communicate with external servers that belong to one or more third-party partners or agencies through an Application Programming Interface ("API") whereby the customer relationship management system can flexibly receive data updates from the one or more third-party partners or agencies. The access protocol that is established may also include a set of alignment rules that determine specific pieces of approved content that are available to the selected customers from the controlled content repository.

While FIG. 14 is described in basic terms regarding its general operation as a controlled content access system, it should be appreciated that such a system is described herein with multiple specific implementations. Such specific implementations can be facilitated through front-end applications in the context of supporting research, development, and initial clinical trial submissions as previously described. Other front-end applications as previously described include manage access and/or distribution of trial documents and reports in support of ongoing clinical trials, materials control and/or manufacturing process controls, communications with medical facilities in support of medical facility operations, and the development and distribution of promotional materials as related to regulatory restricted products such as prescription drugs.

To facilitate the compliance with government regulation, a regulatory compliance engine can be provided to review content and the access protocols and to ensure that only approved content authored by properly authorized individuals and according to required controls can be distributed to permitted possible customers or other content recipients in accordance with government regulations.

Figure 15:
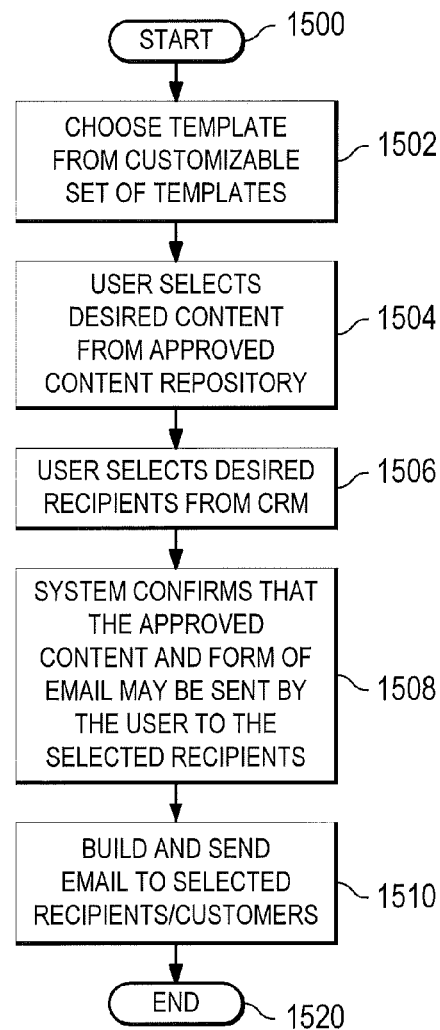
FIG. 15 is a flowchart illustrating the building and sending of approved emails.

Next with regard to FIG. 15, a method for generation of approved email content is described. In particular, FIG. 15 shows at block 1500 the start of the process, after which at block 1502 an email author or prospective sender can choose a template from a set of customizable templates. In this way the email authors or prospective senders do not have to recreate content every time an email campaign is beginning. At block 1504, the user selects the desired content from the approved content repository 102, and the user at block 1506 selects the desired recipients or customers from the CRM database 104.

Still referring to FIG. 15, the system, or more specifically the multichannel processing engine 108 confirms that the approved content and form of email may permissibly be sent by the prospective email sender to the customers or other selected recipients at 1508 based on factors including but not limited to regulatory limitations, customer preferences, demographic information, or the "opt-in" or "opt-out" status of individual customer accounts. Once that has been confirmed in accordance with the access protocol, the multichannel processing engine 108 can begin building and sending the emails in accordance with the user's selections or as modified in accordance with the access protocol, regulator engine, and or other system controls, at 1512. The content contained within the approved email may be checked for accuracy and validity by the system before release to the email server 114. If the email is created when the user is offline, the content contained in the approved emails may be checked again after the user is back online, before they are sent to the email server.

The approved email may be initiated in other scenarios. In one implementation, the approved email may be used to answer a medical inquiry.

Figure 16A:
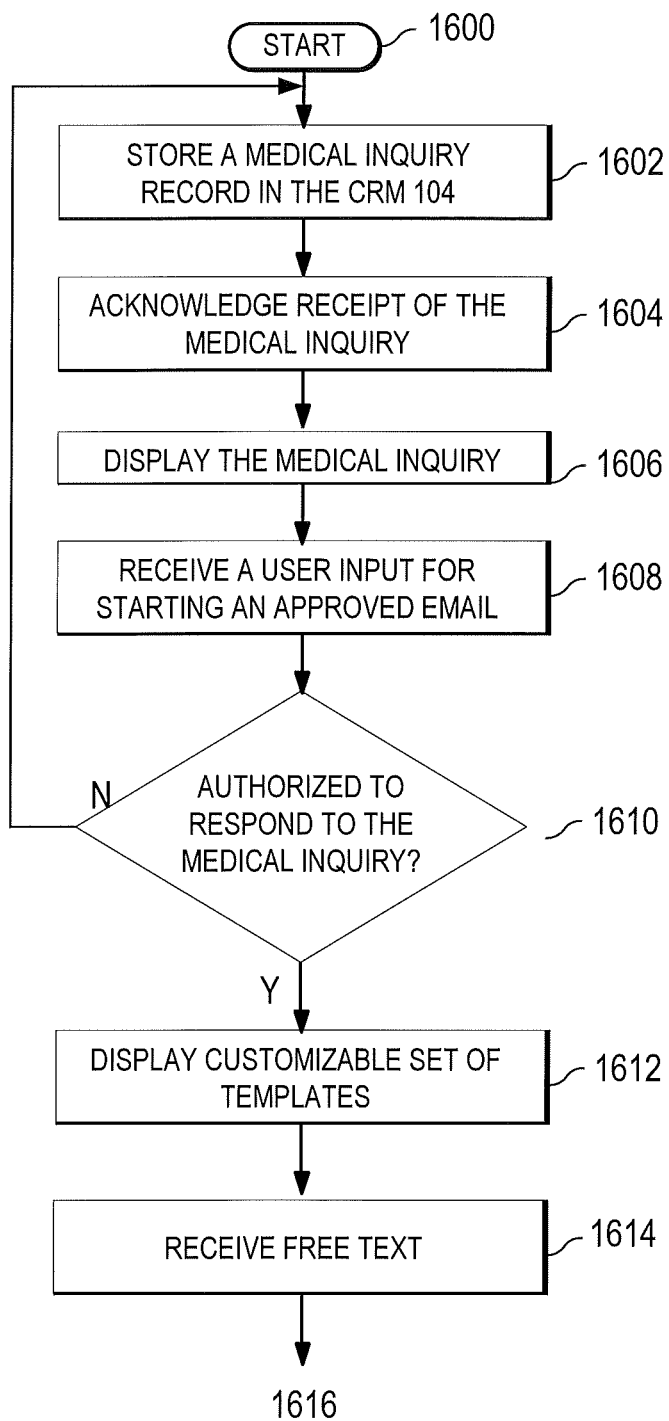
FIGS. 16a-b illustrate a flowchart of a method for building and sending of an approved email in response to a medical inquiry.
Figure 16B:
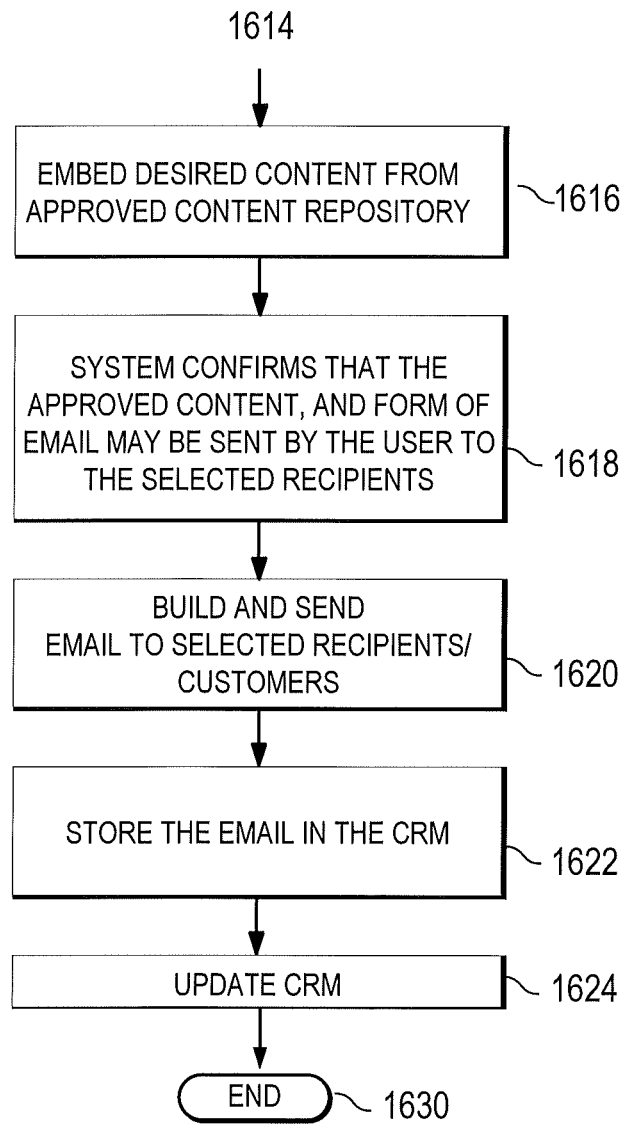
Figure 17:
FIG. 17 illustrates a screenshot of an example user interface for displaying a medical inquiry.
Figure 18:
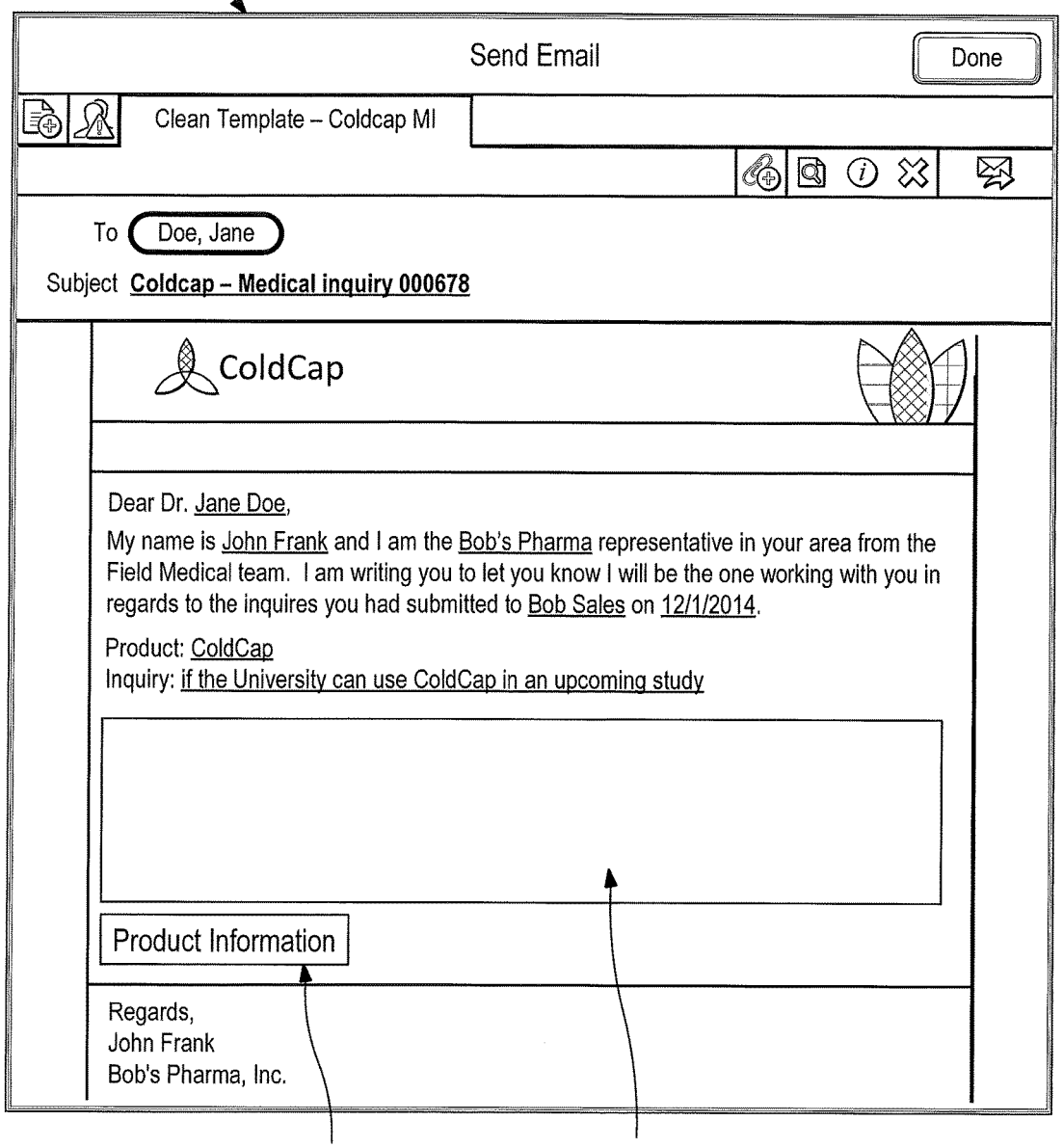
FIG. 18 illustrates a screenshot of an example approved email in response to a medical inquiry.

FIGS. 16a-b illustrate a flowchart of a method for building and sending of an approved email in response to a medical inquiry, and FIGS. 17-18 illustrate examples of user interfaces during the process.

The process may start at 1600.

At 1602, a medical inquiry may be received by a sales representative during his meeting with a physician. The physician may ask if the product ColdCap can be used by the university in an upcoming study. Since the sales representative is not authorized to answer medical inquiries, he may create a medical inquiry record in the customer relationship management subsystem 104, e.g., medical inquiry 0678 shown in FIG. 17, to document the medical inquiry. The medical inquiry record may capture the question from the physician pertaining to a medical topic in a structured way, and may include fields such as the medical inquiry ID, the physician's account information, the physician's preference information, the product involved, the inquiry text, the sales representative receiving it, and the time it was received. The medical inquiry may be received in other scenarios, e.g., by a customer service representative via an email, by a call center agent via a call, or from helpdesk. A record may be created for each medical inquiry received, and all communications related to the medical inquiry may reference that record when they are created and documented, e.g., via a look up field.

At 1604, the sales representative may send an approved email to the physician to acknowledge receipt of the medical inquiry. In one implementation, when the sales representative submits a medical inquiry record, a pop-up window may be displayed, asking the sales representative if he wants to acknowledge receipt of the medical inquiry via an approved email. If the sales representative says yes, an approved email may be generated and displayed. In one embodiment, the acknowledgement may be generated with the method shown in FIG. 15. The template may automatically reference data points from the medical inquiry record, e.g., name of the sales representative, name of the physician, email address of the physician, the time the medical inquiry was received, the medical inquiry ID, and the inquiry text. The sales representative may send the acknowledgement to the physician, and the customer relationship management subsystem 104 may be updated to document that the acknowledgement has been sent.

At 1606, the medical inquiry may be routed to a medical liaison. In one implementation, the medical inquiry may be sent to the medical liaison in an email. Alternatively, the medical liaison may access the medical inquiry in the customer relationship management subsystem 104 and respond with an approved email directly. The medical liaison may be a member on the manufacturer's medical team, and trained and qualified to answer certain medical questions. The medical liaison may have more freedom to write free text than sales representatives in the email. The medical liaison's profile may indicate that he is qualified to answer medical inquiries, authorized to use free text approved email, and can be provided with a template for free text approved email.

At 1608, a user input may be received indicating that the medical liaison wants to respond to the medical inquiry directly from the medical inquiry page 1700 with an approved email, e.g., a click on a "Send Email" link 1701 on page 1700.

At 1610, it may be determined, e.g., by the customer relationship management subsystem 104, if the medical liaison is authorized to respond to the medical inquiry based on regulatory limitations and/or his profile information. If not, the process may return to 1600.

If the medical liaison is authorized to respond to the medical inquire, at 1612, a set of customizable templates may be displayed for him to choose from, and at least one of the templates is for a free text approved email. As shown in FIG. 18, the template 1800 may have one or more fields referencing the medical inquiry, e.g., medical inquiry ID, name of the sales representative, name of the physician, the time the medical inquiry was received, and/or the inquiry text, and these fields may be automatically filled with data pulled from the medical inquiry record when the template is generated, e.g., "000678", "Bob Sales", "Jane Doe", "12/1/2014", and "if the university can use ColdCap in an uncoming study".

The template 1800 may include a free text window 1801 for the medical liaison to enter free text to respond to the medical inquiry. In one implementation, the free text window 1801 may allow the medical liaison to enter free text in plain text or rich text format.

At 1614, free text responding to the medical inquiry may be received at the free text window 1801.

At 1616, the user may select desired content from the approved content repository 102 and embed its link 1802 in the free text approved email, as shown in FIG. 18. The desired content may be, e.g., product information or safety message.

At 1618, in response, the system, or more specifically the multichannel processing engine 108, may determine if the free text approved email, including the selected content, may permissibly be sent by the medical liaison to the physician based on factors including but not limited to keyword check, regulatory limitations, customer preferences, demographic information, or the "opt-in" or "opt-out" status of individual customer accounts. The keyword check may determine if the free text approved email includes any words which are unapproved and need to be blocked, e.g., those wrong, misleading, derogatory, illegal, or offensive. In one implementation, a filter may be used for the keyword checking.

If it is not permissible to send the email by the medical liaison to the physician, the medical liaison may be informed so that he can revise the email and/or change the content.

Once it is determined that the free text approved email can be sent to the physician, the multichannel processing engine 108 can send it at 1620. The content contained within the free text approved email may be checked for accuracy and validity by the system before release to the email server 114. If the email is created when the medical liaison is offline, the content contained in the email may be checked again after he is back online, before the email is sent to the communication server 114.

At 1622, the email sent may be stored in the controlled content repository 102, more specifically, the audit trail storage 150. Alternatively, the email sent may be stored in the customer relationship management subsystem 104

At 1624, the customer relationship management subsystem 104 may be updated, via the CRM updates 111, to record that the email from the medical liaison has been answered.

The process may end at 1630.

Consequently, all communications related to the medical inquiry may be well preserved, because the medical inquiry record is created in the customer relationship management subsystem 104, emails related to the medical inquiry reference the medical inquiry record, the emails are logically linked to the medical inquiry and documented in the CRM system.

The flowcharts do not mean to limit the sequence of the steps. In one example, the controlled content repository 102 may determine in advance, before a template is chosen at 1502, if a piece of content can be sent to a customer and store the result. The result may be stored as a part of metadata for the content in the controlled content repository 102. During the generation of the approved email, the multichannel processing engine may check information in the controlled content repository 102, instead of the customer relationship management subsystem 104, to decide if a piece of content can be sent to a customer.

While various embodiments have been described above, it should be understood that they have been presented by way of example only, and not limitation. Thus, the breadth and scope of a preferred embodiment should not be limited by any of the above described exemplary embodiments, but should be defined only in accordance with the claims and their equivalents for any patent that issues claiming priority from the present provisional patent application.

For example, although the embodiments are described with a customer relationship management subsystem 104, the customer information and content may be from other types of information management systems, e.g., a Closed Loop Marketing (CLM) system. In addition, the multichannel processing engine 108 is shown to communicate with only one customer relationship management subsystem 104 in the drawings, but it may communicate with more customer relationship management subsystems. For example, as referred to herein, a machine or engine may be a virtual machine, computer, node, instance, host, or machine in a networked computing environment. Also as referred to herein, a networked computing environment is a collection of machines connected by communication channels that facilitate communications between machines and allow for machines to share resources. Network may also refer to a communication medium between processes on the same machine. Also as referred to herein, a server is a machine deployed to execute a program operating as a socket listener and may include software instances.

In all descriptions of "servers" or other computing devices herein, whether or not the illustrations of those servers or other computing devices similarly show a server-like illustration in the figures, it should be understood that any such described servers or computing devices will similarly perform their described functions in accordance with computer-readable instructions stored on a computer-readable media that are connected thereto.

Resources may encompass any types of resources for running instances including hardware (such as servers, clients, mainframe computers, networks, network storage, data sources, memory, central processing unit time, scientific instruments, and other computing devices), as well as software, software licenses, available network services, and other non-hardware resources, or a combination thereof.

A networked computing environment may include, but is not limited to, computing grid systems, distributed computing environments, cloud computing environment, etc. Such networked computing environments include hardware and software infrastructures configured to form a virtual organization comprised of multiple resources which may be in geographically disperse locations.

The approved content may be in any format, e.g., text, audio, video, picture, multimedia, or PDF.

Various terms used herein have special meanings within the present technical field. Whether a particular term should be construed as such a "term of art," depends on the context in which that term is used. "Connected to," "in communication with," or other similar terms should generally be construed broadly to include situations both where communications and connections are direct between referenced elements or through one or more intermediaries between the referenced elements, including through the Internet or some other communicating network. "Network," "system," "environment," and other similar terms generally refer to networked computing systems that embody one or more aspects of the present disclosure. These and other terms are to be construed in light of the context in which they are used in the present disclosure and as those terms would be understood by one of ordinary skill in the art would understand those terms in the disclosed context. The above definitions are not exclusive of other meanings that might be imparted to those terms based on the disclosed context.

Words of comparison, measurement, and timing such as "at the time," "equivalent," "during," "complete," and the like should be understood to mean "substantially at the time," "substantially equivalent," "substantially during," "substantially complete," etc., where "substantially" means that such comparisons, measurements, and timings are practicable to accomplish the implicitly or expressly stated desired result.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Technical Field," such claims should not be limited by the language chosen under this heading to describe the so-called technical field. Further, a description of a technology in the "Background" is not to be construed as an admission that technology is prior art to any invention(s) in this disclosure. Neither is the "Brief Summary" to be considered as a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

What is claimed is:

1. A machine-implemented method for generating approved electronic messages, the method comprising:
   establishing an access protocol for a controlled content repository, whereby approved content is stored in the controlled content repository and is accessible according to the access protocol, and whereby the access protocol comprises at least one set of alignment rules for determining if a first item of approved content within the controlled content repository can be made available to a first customer via an electronic message;
   aligning, by a computing device, the approved content within the controlled content repository with information from an information management system;
   providing the first item of approved content for selection by a sender after a determination that the first item of approved content is authorized to be made available to the first customer in accordance with the at least one set of alignment rules; and
   enabling generation of an electronic message for sending the provided first item of approved content to the first customer, wherein the electronic message responds to a medical inquiry from the first customer.

2. The method of claim 1, wherein the information management system is a customer relationship management (CRM) system or a closed loop marketing (CLM) system.

3. The method of claim 1, further comprising: creating an object for the medical inquiry in the information management system.

4. The method of claim 3, further comprising: routing the medical inquiry to the sender.

5. The method of claim 4, further comprising: displaying the medical inquiry on a user interface, and receiving an input on the user interface for answering the medical inquiry with the electronic message.

6. The method of claim 5, further comprising: providing a template for the electronic message, wherein the template is pre-generated with data pulled from the object for the medical inquiry in the information management system.

7. The method of claim 6, wherein the template has at least one customizable area for receiving free text answering the medical inquiry.

8. The method of claim 6, wherein the free text is in rich text format.

9. The method of claim 6, further comprising: determining that the sender is authorized to enter free text answering the medical inquiry to the at least one customizable area by checking the sender's profile information.

10. The method of claim 6, further comprising: receiving free text answering the medical inquiry at the at least one customizable area, and determining if the free text includes a first unapproved word.

11. The method of claim 10, further comprising: blocking the electronic message and informing the user if the free text includes the first unapproved word.

12. The method of claim 10, further comprising: filtering the free text for the first unapproved word.

13. The method of claim 6, further comprising: determining if the electronic message may permissibly be sent by the sender to the first customer according to a limitation in the information management system.

14. The method of claim 13, wherein the limitation in the information management system comprises a regulatory limitation, preferences of the first customer, and profile information of the first customer.

15. The method of claim 4, further comprising:
   sending the electronic message to the first customer; and
   updating the information management system with the sending of the electronic message.

16. The method of claim 1, wherein the controlled content repository is adapted to provide development and distribution of promotional materials as related to regulatory restricted products.

17. The method of claim 16, wherein the regulatory restricted products are prescription drugs.

18. A system for generating approved electronic messages, comprising:
   a controlled content repository for storing approved content according to an access protocol, wherein the access protocol is based on regulatory restrictions, and comprises at least one set of alignment rules for determining, by a computing device, if a first piece of approved content within the controlled content repository can be made available to a first customer via an electronic message;
   an information management system for storing an object for a medical inquiry from the first customer; and
   an approved electronic message generator, coupled to the controlled content repository and the information management system, coupled to an application over a network, and generating an electronic message for answering the medical inquiry from the first customer, wherein the electronic message comprises data pulled from the object for the medical inquiry.

19. The system of claim 18, further comprising a keyword filter for determining if free text in the electronic message includes a first unapproved word.

20. The system of claim 18, further comprising: a regulatory compliance engine for checking that the electronic message is in compliance with government regulations.

* * * * *